(12) United States Patent
Zucca et al.

(10) Patent No.: US 8,404,472 B2
(45) Date of Patent: Mar. 26, 2013

(54) SYSTEM FOR PRODUCING AROMATIC MOLECULES BY BIOCONVERSION

(75) Inventors: Joseph Zucca, Grasse (FR); Fanny Lambert, Pegomas (FR); Jean Mane, Grasse (FR); Frédérique Ness, Bordeaux (FR); Michel Aigle, Villerbanne (FR)

(73) Assignee: V. Mane Fils, Bar sur Loup (FR)

( * ) Notice: Subject to any disclaimer, the term of this patent is extended or adjusted under 35 U.S.C. 154(b) by 776 days.

(21) Appl. No.: 12/281,405

(22) PCT Filed: Feb. 28, 2007

(86) PCT No.: PCT/FR2007/000364
§ 371 (c)(1),
(2), (4) Date: Sep. 2, 2008

(87) PCT Pub. No.: WO2007/099230
PCT Pub. Date: Sep. 7, 2007

(65) Prior Publication Data
US 2010/0028963 A1 Feb. 4, 2010

(30) Foreign Application Priority Data
Mar. 1, 2006 (FR) .................................... 06 01838

(51) Int. Cl.
| | |
|---|---|
| C12N 9/02 | (2006.01) |
| C12N 1/20 | (2006.01) |
| C12N 1/14 | (2006.01) |
| C12N 1/00 | (2006.01) |
| C12N 15/00 | (2006.01) |
| C12P 7/00 | (2006.01) |
| C12P 7/02 | (2006.01) |
| C07H 21/04 | (2006.01) |
| C07H 21/02 | (2006.01) |

(52) U.S. Cl. ..................... 435/189; 435/243; 435/254.2; 435/252.3; 435/440; 435/132; 435/155; 536/23.2; 536/23.1

(58) Field of Classification Search .................. None
See application file for complete search history.

(56) References Cited

U.S. PATENT DOCUMENTS
6,306,625 B1 * 10/2001 Jacobs et al. ............... 435/69.9

FOREIGN PATENT DOCUMENTS
| | | |
|---|---|---|
| EP | 453 368 | 10/1991 |
| EP | 606 441 | 7/1994 |
| EP | 0804606 | 11/1997 |
| WO | 96/08576 | 3/1996 |
| WO | 0061721 | 10/2000 |
| WO | 01/55342 | 8/2001 |

OTHER PUBLICATIONS

Branden et al. Introduction to Protein Structure, Garland Publishing Inc., New York, p. 247, 1991.*
Mattevi et al. UniProt Database—P56216—1998.*
Sambrook et al. Molecular Cloning, 1989, Cold Spring Harbor Laboratory Press, pp. 8.46-8.52 and pp. 11.2-11.*
EMBL-EBI Database. PDB ID: 1dzn. 2000.*
EMBL-EBI Database. PDB ID: 1e0y. 2000.*
EMBL-EBI Database. PDB ID: 1e8g. 2000.*
BRENDA Database. EC 1.1.3.38. Retrieved from the internet via http://www.brenda-enzymes.info/php/result_flat.php4?ecno=1.1.3.38 on Dec. 10, 2011.*
Overhage Joerg et al., "Highly efficient biotransformation of eugenol to ferulic acid and further conversion to vanillin in recombinant strains of *Escherichia coli*", Applied and Environmental Microbiology, vol. 69, No. 11, Nov. 2003, pp. 6569-6576.
Benen Jacques et al., "Molecular cloning, sequencing, and heterologous expression of the vaoA gene from *Penicillium simplicissimum* CBS 170.90 encoding vanillyl-alcohol oxidase", Journal of Biological Chemistry, vol. 273, No. 14, Apr. 3, 1998, pp. 7865-7872.
Gueldner U. et al., "A new efficient gene disruption cassette for repeated use in budding yeast", Nucleic Acids Research, Oxford Univ. Press, vol. 24, No. 13, 1996, pp. 2519-2524.
Bonneaud N. et al., "A Family of Low and High Copy Replicative Integrative and Single-Stranded *Saccharomyces-cerevisiae* and *Escherichia-coli* Shuttle Vectors", Yeast, vol. 7, No. 6, 1991, pp. 609-616.
Rapid Translation System RTS pIVEX His-tag vector Set, Cat. No. 3 252 538, Roche Molecular Biomedicals, May 2001, pp. 1-6.
Overhage Joerg et al., "Biotransformation of eugenol to ferulic acid by a recombinant strain of *Ralstonia eutropha* H16", Applied and Environmental Microbiology, vol. 68, No. 9, Sep. 2002, pp. 4315-4321.
Overhage Joerg et al., "Biotransformation of eugenol to vanillin by a mutant of *Pseudomonas* sp. strain HR199 constructed by disruption of the vanillin dehydrogenase (vdh) gene", Applied Microbiology and Biotechnology, vol. 52, No. 6, Nov. 1999, pp. 820-838.

* cited by examiner

*Primary Examiner* — Yong Pak
(74) *Attorney, Agent, or Firm* — Young & Thompson

(57) ABSTRACT

Yeast comprising at least one gene encoding vanillyl alcohol oxidase, the sequence of which is the sequence SEQ ID No. 1 or any sequence at least 70%, preferably 80%, very preferably 90% homologous to the sequence SEQ ID No. 1, and methods for producing coniferyl alcohol, ferulic acid and vanillin.

18 Claims, 3 Drawing Sheets

Figure 1:
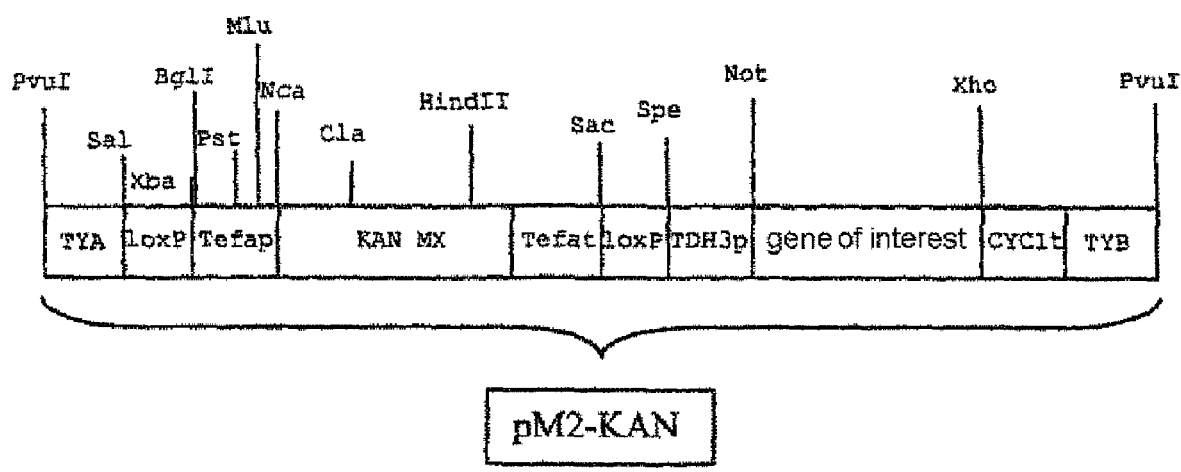

M: Molecular size marker
S: Soluble fraction after centrifugation
FT: Fraction not retained on Ni-NTA
E: Elution fraction from the Ni-NTA resin

SEQUENCE LISTING

<160> NUMBER OF SEQ ID NOS: 15

<210> SEQ ID NO 1
<211> LENGTH: 1734
<212> TYPE: DNA
<213> ORGANISM: P. simplicissimum

<400> SEQUENCE: 1

```
atgagcggcc gctcaaagac tcaagagttc agaccattga ctttgccacc aaagttgtct      60
ttgtcagact tcaacgagtt cattcaagac attattagaa ttgttggttc agagaacgtt     120
gaggttattt catctaagga ccaaattgtt gacggttctt atatgaagcc aactcatact     180
catgacccac atcatgttat ggaccaagac tatttcttgg cttctgctat tgttgctcca     240
agaaacgttg ctgacgttca atctattgtt ggtttggcta acaagttctc tttcccattg     300
tggccaattt caattggtag aaactctggt tatggtggtc ctgctcccg  ggtttcaggt     360 tctgttgttt tggacatggg taagaacatg aacagagttt tggaggttaa cgttgaaggt     420
gcttattgtg ttgttgaacc aggtgttact tatcatgact tgcataacta tttggaggct     480
aacaacttga gagacaaatt gtggttagac gttccagatc taggtggtgg ttctgttttg     540
ggtaacgctg ttgaaagagg tgttggttat actccatacg gtgatcattg gatgatgcat     600
tctggtatgg aggttgtttt ggctaacggt gagttgttaa gaactggtat gggtgcttta     660
ccagacccaa aaagaccaga gactatgggt ttgaagccag aagatcaacc atggtctaag     720
attgctcatt tgttcccata cggtttcggt ccatatattg atggtttgtt ctctcaatct     780
aacatgggta ttgttactaa gattggtatt tggttaatgc caaacccagg tggttatcaa     840
tcttatttga ttactttacc aaaggatggt gacttgaagc aagctgttga cattattaga     900
ccattgagat aggtatggc  tttgcaaaac gttccaacta ttagacatat tttattggat     960
gctgctgttt tgggtgacaa gagatcatat tcttcaaaaa ctgagccatt gtctgacgag    1020
gagttggaca agattgctaa gcaattgaac ttgggtagat ggaactttta tggtgctttg    1080
tatggtccag aaccaattag aagagttttg tgggagacta ttaaagatgc tttctctgct    1140
attccaggtg ttaagttcta ttttccagaa gatactccag agaactctgt tttgagagtt    1200
```

```
agagacaaga ctatgcaagg tattccaact tatgacgagt taaaatggat tgactggttg    1260
ccaaacggtg ctcatttgtt cttctctcca attgctaagg tttctggtga agacgctatg    1320
atgcaatatg ctgttactaa aaagagatgt caagaggctg gtttggactt cattggtact    1380
tttactgttg gcatgcgtga gatgcatcat attgttgta ttgttttcaa caagaaggac    1440
ttgattcaaa agagaaaggt tcaatggttg atgagaactt tgattgatga ctgtgctgct    1500
aatggttggg gtgagtatag aactcatttg gctttcatgg accaaattat ggagacttat    1560
aactggaaca actcttcatt cttgagattc aacgaggttt tgaagaacgc tgttgatcca    1620
aacggtatta ttgctccagg taagtcaggt gtttggccat ctcaatattc tcatgttact    1680
tggaagctcg agcgagctcc cgggggggt tctcatcatc atcatcatca ttaa           1734

<210> SEQ ID NO 2
<211> LENGTH: 29
<212> TYPE: DNA
<213> ORGANISM: artificial
<220> FEATURE:
<223> OTHER INFORMATION: synthetic nucleotide

<400> SEQUENCE: 2
gcggccgcgg atcccaattg cgactcgag                                        29

<210> SEQ ID NO 3
<211> LENGTH: 34
<212> TYPE: DNA
<213> ORGANISM: bacteriophage P1

<400> SEQUENCE: 3
ataacttcgt ataatgtatg ctatacgaag ttat                                  34

<210> SEQ ID NO 4
<211> LENGTH: 149
<212> TYPE: DNA
<213> ORGANISM: S. cerevisiae

<400> SEQUENCE: 4
ctgtgcttcg gttacttcta aggaagtcca cacaaatcaa gatccgttag acgtttcagc    60
ttccaaaaca gaagaatgtg agaaggcttc cactaaggct aactctcaac agacaacaac   120
acctgcttca tctgctgttc cagagaacc                                      149

<210> SEQ ID NO 5
<211> LENGTH: 153
<212> TYPE: DNA
<213> ORGANISM: S. cerevisiae

<400> SEQUENCE: 5
acctgataca agaacttaac aagaaaccaa ttattaaagg cttacttact gatagtagat    60
caacgatcag tataattaag tctacaaatg aagagaaatt tagaaacaga ttttttggca   120
caaaggcaat gagacttaga gatgaagtat cag                                 153

<210> SEQ ID NO 6
<211> LENGTH: 596
<212> TYPE: DNA
<213> ORGANISM: S. cerevisiae

<400> SEQUENCE: 6
tcaaaaaact agtcttttaa ttctgctgta acccgtacat gcccaaaata ggggcgggt    60 tacacagaat atataacatc gtaggtgtct gggtgaacag tttattcctg gcatccacta   120
```

-continued

```
aatataatgg agcccgcttt ttaagctggc atccagaaaa aaaaagaatc ccagcaccaa    180
aatattgttt tcttcaccaa ccatcagttc ataggtccat tctcttagcg caactacaga    240 gaacagggc acaaacaggc aaaaaacggg cacaacctca atggagtgat gcaacctgcc    300
tggagtaaat gatgacacaa ggcaattcac ccacgcatgt atctatctca ttttcttaca    360
ccttctatta ccttctgctc tctctgattt ggaaaaagct gaaaaaaaag gttgaaacca    420
gttccctgaa attattcccc tacttgacta ataagtatat aaagacggta ggtattgatt    480
gtaattctgt aaatctattt cttaaacttc ttaaattcta cttttatagt tagtcttttt    540
tttagtttta aaacaccaag aacttagttt cgaataaaca cacataaaca aacaaa       596
```

<210> SEQ ID NO 7
<211> LENGTH: 204
<212> TYPE: DNA
<213> ORGANISM: S. cerevisiae

<400> SEQUENCE: 7

```
acaggcccct tttcctttgt cgatctcatg taattagtta tgtcacgctt acattcacgc     60
cctcctccca catccgctct aaccgaaaag gaaggagtta gacaacctga agtctaggtc    120
cctatttatt tttttaata gttatgttag tattaagaac gttatttata tttcaaattt    180
ttcttttttt tctgtacaaa cgcg                                          204
```

<210> SEQ ID NO 8
<211> LENGTH: 383
<212> TYPE: DNA
<213> ORGANISM: A. gossypii

<400> SEQUENCE: 8

```
gtttagcttg cctcgtcccc gccgggtcac ccggccagcg acatggaggc ccagaatacc     60
ctccttgaca gtcttgacgt gcgcagctca ggggcatgat gtgactgtcg cccgtacatt    120
tagcccatac atccccatgt ataatcattt gcatccatac attttgatgg ccgcacggcg    180
cgaagcaaaa attacggctc ctcgctgcag acctgcgagc agggaaacgc tcccctcaca    240
gacgcgttga attgtcccca cgccgcgccc ctgtagagaa atataaaagg ttaggatttg    300
ccactgaggt tcttctttca tatacttcct tttaaaatct tgctaggata cagttctcac    360
atcacatccg aacataaaca acc                                          383
```

<210> SEQ ID NO 9
<211> LENGTH: 244
<212> TYPE: DNA
<213> ORGANISM: A. gossypii

<400> SEQUENCE: 9

```
tcagtactga caataaaaag attcttgttt tcaagaactt gtcatttgta tagttttttt     60
atattgtagt tgttctattt taatcaaatg ttagcgtgat ttatattttt tttcgcctcg    120
acatcatctg cccagatgcg aagttaagtg cgcagaaagt aatatcatgc gtcaatcgta    180
tgtgaatgct ggtcgctata ctgctgtcga ttcgatacta acgccgccat ccagtgtcga    240
aaac                                                                244
```

<210> SEQ ID NO 10
<211> LENGTH: 810
<212> TYPE: DNA
<213> ORGANISM: E. coli

<400> SEQUENCE: 10

-continued

```
atgggtaagg aaaagactca cgtttcgagg ccgcgattaa attccaacat ggatgctgat      60
ttatatgggt ataaatgggc tcgcgataat gtcgggcaat caggtgcgac aatctatcga     120
ttgtatggga agcccgatgc gccagagttg tttctgaaac atggcaaagg tagcgttgcc     180
aatgatgtta cagatgagat ggtcagacta aactggctga cggaatttat gcctcttccg     240
accatcaagc atttatccg tactcctgat gatgcatggt tactccacca tgcgatcccc     300
ggcaaaacag cattccaggt attagaagaa tatcctgatt caggtgaaaa tattgttgat     360
gcgctggcag tgttcctgcg ccggttgcat tcgattcctg tttgtaattg tccttttaac     420
agcgatcgcg tatttcgtct cgctcaggcg caatcacgaa tgaataacgg tttggttgat     480
gcgagtgatt ttgatgacga gcgtaatggc tggcctgttg aacaagtctg aaagaaatg     540
cataagcttt tgccattctc accggattca gtcgtcactc atggtgattt ctcacttgat     600
aaccttattt ttgacgaggg gaaattaata ggttgtattg atgttggacg agtcggaatc     660
gcagaccgat accaggatct tgccatccta tggaactgcc tcggtgagtt ttctccttca     720
ttacagaaac ggcttttca aaaatatggt attgataatc ctgatatgaa taaattgcag     780
tttcatttga tgctcgatga gttttctaa                                       810

<210> SEQ ID NO 11
<211> LENGTH: 3745
<212> TYPE: DNA
<213> ORGANISM: artificial
<220> FEATURE:
<223> OTHER INFORMATION: expression system comprising synthetic VAO gene

<400> SEQUENCE: 11
gaattccagc tgtgcttcgg ttacttctaa ggaagtccac acaaatcaag atccgttaga      60
cgtttcagct tccaaaacag aagaatgtga gaaggcttcc actaaggcta actctcaaca     120
gacaacaaca cctgcttcat ctgctgttcc agagaaccga taacttcgta taatgtatgc     180
tatacgaagt tatatgggta aggaaaagac tcacgtttcg aggccgcgat taaattccaa     240
catggatgct gatttatatg gtataaatg gctcgcgat aatgtcgggc aatcaggtgc     300
gacaatctat cgattgtatg ggaagcccga tgcgccagag ttgtttctga acatggcaa     360
aggtagcgtt gccaatgatg ttacagatga gatggtcaga ctaaactggc tgacggaatt     420
tatgcctctt ccgaccatca agcatttat ccgtactcct gatgatgcat ggttactcac     480
cactgcgatc cccggcaaaa cagcattcca ggtattagaa gaatatcctg attcaggtga     540
aaatattgtt gatgcgctgg cagtgttcct gcgccggttg cattcgattc ctgtttgtaa     600
ttgtcctttt aacagcgatc gcgtatttcg tctcgctcag gcgcaatcac gaatgaataa     660
cggtttggtt gatgcgagtg attttgatga cgagcgtaat ggctggcctg ttgaacaagt     720
ctggaaagaa atgcataagc ttttgccatt ctcaccggat tcagtcgtca ctcatggtga     780
tttctcactt gataacctta ttttgacga ggggaaatta ataggttgta ttgatgttgg     840
acgagtcgga atcgcagacc gataccagga tcttgccatc ctatggaact gcctcggtga     900
gttttctcct tcattacaga aacggctttt tcaaaaatat ggtattgata atcctgatat     960
gaataaattg cagtttcatt tgatgctcga tgagtttttc taacaaccct aatataact    1020
tcgtataatg tatgctatac gaagttatta ggtcaaaaaa ctagtctttt aattctgctg    1080
taacccgtac atgcccaaaa tagggggcgg gttacacaga atatataaca tcgtaggtgt    1140
ctgggtgaac agtttattcc tggcatccac taaatataat ggagcccgct ttttaagctg    1200
gcatccagaa aaaaaagaa tcccagcacc aaaatattgt tttcttcacc aaccatcagt    1260
```

```
tcataggtcc attctcttag cgcaactaca gagaacaggg gcacaaacag gcaaaaaacg    1320
ggcacaacct caatggagtg atgcaacctg cctggagtaa atgatgacac aaggcaattc    1380
acccacgcat gtatctatct cattttctta caccttctat taccttctgc tctctctgat    1440
ttggaaaaag ctgaaaaaaa aggttgaaac cagttccctg aaattattcc cctacttgac    1500
taataagtat ataaagacgg taggtattga ttgtaattct gtaaatctat ttcttaaact    1560
tcttaaattc tacttttata gttagtcttt ttttagttt taaaacacca agaacttagt     1620
ttcgaataaa cacacataaa caaacaaaat gagcggccgc tcaaagactc aagagttcag    1680
accattgact ttgccaccaa agttgtcttt gtcagacttc aacgagttca ttcaagacat    1740
tattagaatt gttggttcag agaacgttga ggttatttca tctaaggacc aaattgttga    1800
cggttcttat atgaagccaa ctcatactca tgacccacat catgttatgg accaagacta    1860
tttcttggct tctgctattg ttgctccaag aaacgttgct gacgttcaat ctattgttgg    1920
tttggctaac aagttctctt tcccattgtg gccaatttca attggtagaa actctggtta    1980
tggtggtgct gctccccggg tttcaggttc tgttgttttg gacatgggta agaacatgaa    2040
cagagttttg gaggttaacg ttgaaggtgc ttattgtgtt gttgaaccag gtgttactta    2100
tcatgacttg cataactatt tggaggctaa caacttgaga gacaaattgt ggttagacgt    2160
tccagatcta ggtggtggtt ctgtttttggg taacgctgtt gaaagaggtg ttggttatac    2220
tccatacggt gatcattgga tgatgcattc tggtatggag gttgttttgg ctaacggtga    2280
gttgttaaga actggtatgg gtgctttacc agacccaaaa agaccagaga ctatgggttt    2340
gaagccagaa gatcaaccat ggtctaagat tgctcatttg ttcccatacg gtttcggtcc    2400
atatattgat ggtttgttct ctcaatctaa catgggtatt gttactaaga ttggtatttg    2460
gttaatgcca aacccaggtg gttatcaatc ttatttgatt actttaccaa aggatggtga    2520
cttgaagcaa gctgttgaca ttattagacc attgagatta ggtatggctt tgcaaaacgt    2580
tccaactatt agacatattt tattggatgc tgctgttttg ggtgacaaga gatcatattc    2640
ttcaaaaact gagccattgt ctgacgagga gttggacaag attgctaagc aattgaactt    2700
gggtagatgg aacttttatg gtgctttgta tggtccagaa ccaattagaa gagttttgtg    2760
ggagactatt aaagatgctt tctctgctat tccaggtgtt aagttctatt ttccagaaga    2820
tactccagag aactctgttt tgagagttag agacaagact atgcaaggta ttccaactta    2880
tgacgagtta aaatggattg actggttgcc aaacggtgct catttgttct tctctccaat    2940
tgctaaggtt tctggtgaag acgctatgat gcaatatgct gttactaaaa agagatgtca    3000
agaggctggt ttggacttca ttggtacttt tactgttggc atgcgtgaga tgcatcatat    3060
tgtttgtatt gttttcaaca agaaggactt gattcaaaag agaaaggttc aatggttgat    3120
gagaactttg attgatgact gtgctgctaa tggttggggt gagtatagaa ctcatttggc    3180
tttcatggac caaattatgg agacttataa ctggaacaac tcttcattct tgagattcaa    3240
cgaggttttg aagaacgctg ttgatccaaa cggtattatt gctccaggta agtcaggtgt    3300
ttggccatct caatattctc atgttacttg gaagctcgag catcatcatc atcatcatga    3360
attgcgactc gagtaataaa caggcccctt ttcctttgtc gatctcatgt aattagttat    3420
gtcacgctta cattcacgcc ctcctcccac atccgctcta accgaaaagg aaggagttag    3480
acaacctgaa gtctaggtcc ctatttattt tttttaatag ttatgttagt attaagaacg    3540
ttatttatat ttcaaatttt tcttttttttt ctgtacaaac gcgacctgat acaagaactt    3600
aacaagaaac caattattaa aggcttactt actgatagta gatcaacgat cagtataatt    3660
```

| | |
|---|---|
| aagtctacaa atgaagagaa atttagaaac agatttttg gcacaaaggc aatgagactt | 3720 |
| agagatgaag tatcagctgc tgcag | 3745 |

<210> SEQ ID NO 12
<211> LENGTH: 3833
<212> TYPE: DNA
<213> ORGANISM: artificial
<220> FEATURE:
<223> OTHER INFORMATION: synthetic NAT1-CRE sequence

<400> SEQUENCE: 12

| | |
|---|---|
| ggatctgttt agcttgcctc gtccccgccg ggtcacccgg ccagcgacat ggaggcccag | 60 |
| aatacccctcc ttgacagtct tgacgtgcgc agctcagggg catgatgtga ctgtcgcccg | 120 |
| tacatttagc ccatacatcc ccatgtataa tcatttgcat ccatacattt tgatggccgc | 180 |
| acggcgcgaa gcaaaaatta cggctcctcg ctgcagacct gcgagcaggg aaacgctccc | 240 |
| ctcacagacg cgttgaattg tccccacgcc gcgcccctgt agagaaatat aaaaggttag | 300 |
| gatttgccac tgaggttctt ctttcatata cttcctttta aaatcttgct aggatacagt | 360 |
| tctcacatca catccgaaca taaacaacca tgaccactct tgacgacacg gcttaccggt | 420 |
| accgcaccag tgtcccgggg gacgccgagg ccatcgaggc actggatggg tccttcacca | 480 |
| ccgacaccgt cttccgcgtc accgccaccg gggacggctt caccctgcgg gaggtgccgg | 540 |
| tggacccgcc cctgaccaag gtgttccccg acgacgaatc ggacgacgaa tcggacgccg | 600 |
| gggaggacgg cgacccggac tcccggacgt tcgtcgcgta cggggacgac ggcgacctgg | 660 |
| cgggcttcgt ggtcgtctcg tactccggct ggaaccgccg gctgaccgtc gaggacatcg | 720 |
| aggtcgcccc ggagcaccgg gggcacgggg tcgggcgcgc gttgatgggg ctcgcgacgg | 780 |
| agttcgcccg cgagcggggc gccgggcacc tctggctgga ggtcaccaac gtcaacgcac | 840 |
| cggcgatcca cgcgtaccgg cggatggggt tcacccctct cggcctggac accgccctgt | 900 |
| acgacggcac cgcctcggac ggcgagcagg cgctctacat gagcatgccc tgcccctaat | 960 |
| cagtactgac aataaaaaga ttcttgtttt caagaacttg tcatttgtat agtttttta | 1020 |
| tattgtagtt gttctatttt aatcaaatgt tagcgtgatt tatatttttt ttcgcctcga | 1080 |
| catcatctgc ccagatgcga agttaagtgc gcagaaagta atatcatgcg tcaatcgtat | 1140 |
| gtgaatgctg gtcgctatac tgctgtcgat tcgatactaa cgccgccatc cagtgtcgaa | 1200 |
| aacgagctcg aattcactgg ccgtcgtttt acaacgtcgt gactgggaaa accctggcgt | 1260 |
| tacccaactt aatcgccttg cagcacatcc ccctttcgcc agctggcacg acaggtttcc | 1320 |
| cgactggaaa gcgggcagtg agcgcaacgc aattaatgtg agttacctca ctcattaggc | 1380 |
| accccaggct ttacacttta tgcttccggc tcctatgttg tgtggaattg tgagcggata | 1440 |
| acaatttcac acaggaaaca gctatgacca tgattacgcc aagcgcgcaa ttaaccctca | 1500 |
| ctaaagggaa caaagctgg agctctagta cggattagaa gccgccgagc gggtgacagc | 1560 |
| cctccgaagg aagactctcc tccgtgcgtc ctcgtcttca ccggtcgcgt tcctgaaacg | 1620 |
| cagatgtgcc tcgcgccgca ctgctccgaa caataaagat tctacaatac tagcttttat | 1680 |
| ggttatgaag aggaaaaatt ggcagtaacc tggccccaca aaccttcaaa tgaacgaatc | 1740 |
| aaattaacaa ccataggatg ataatgcgat tagtttttta gccttatttc tggggtaatt | 1800 |
| aatcagcgaa gcgatgattt tgatctatt aacagatata taaatgcaaa aactgcataa | 1860 |
| ccactttaac taatactttc aacattttcg gtttgtatta cttcttattc aaatgtaata | 1920 |
| aaagtatcaa caaaaaattg ttaatatacc tctatacttt aacgtcaagg agaaaaaacc | 1980 |

| | |
|---|---|
| ccggattcta gaactagtgg atcccccggg ctgcaggaat tcgatatcaa gcttatcgat | 2040 |
| accgtcgagg ggcagagccg atcctgtaca ctttacttaa aaccattatc tgagtgttaa | 2100 |
| atgtccaatt tactgaccgt acaccaaaat ttgcctgcat taccggtcga tgcaacgagt | 2160 |
| gatgaggttc gcaagaacct gatggacatg ttcaggatc gccaggcgtt ttctgagcat | 2220 |
| acctggaaaa tgcttctgtc cgtttgccgg tcgtgggcgg catggtgcaa gttgaataac | 2280 |
| cggaaatggt ttcccgcaga acctgaagat gttcgcgatt atcttctata tcttcaggcg | 2340 |
| cgcggtctgg cagtaaaaac tatccagcaa catttgggcc agctaaacat gcttcatcgt | 2400 |
| cggtccgggc tgccacgacc aagtgacagc aatgctgttt cactggttat gcggcggatc | 2460 |
| cgaaaagaaa acgttgatgc cggtgaacgt gcaaacagg ctctagcgtt cgaacgcact | 2520 |
| gatttcgacc aggttcgttc actcatgaa aatagcgatc gctgccagga tatacgtaat | 2580 |
| ctggcatttc tggggattgc ttataacacc ctgttacgta tagccgaaat tgccaggatc | 2640 |
| agggttaaag atatctcacg tactgacggt gggagaatgt taatccatat tggcagaacg | 2700 |
| aaaacgctgg ttagcaccgc aggtgtagag aaggcactta gcctgggggt aactaaactg | 2760 |
| gtcgagcgat ggatttccgt ctctggtgta gctgatgatc cgaataacta cctgttttgc | 2820 |
| cgggtcagaa aaaatggtgt tgccgcgcca tctgccacca gccagctatc aactcgcgcc | 2880 |
| ctggaaggga ttttttgaagc aactcatcga ttgatttacg gcgctaagga tgactctggt | 2940 |
| cagagatacc tggcctggtc tggacacagt gcccgtgtcg gagccgcgcg agatatggcc | 3000 |
| cgcgctggag tttcaatacc ggagatcatg caagctggtg gctggaccaa tgtaaatatt | 3060 |
| gtcatgaact atatccgtac cctggatagt gaaacagggg caatggtgcg cctgctggaa | 3120 |
| gatggcgatt agccattaac gcgtaaatga ttgctataat tatttgatat ttatggtgac | 3180 |
| atatgagaaa ggatttcaac atcgacggaa aatatgtagt gctgtctgta agcactaata | 3240 |
| ttcagtcgcc agccgtcatt gtcactgtaa agctgagcga tagaatgcct gatattgact | 3300 |
| caatatccgt tgcgtttcct gtcaaaagta tgcgtagtgc tgaacatttc gtgatgaatg | 3360 |
| ccaccgagga agaagcacgg cgcggttttg ctaaagtgat gtctgagttt ggcgaactct | 3420 |
| tgggtaaggt tggaattgtc gacctcgagt catgtaatta gttatgtcac gcttacattc | 3480 |
| acgccctccc cccacatccg ctctaaccga aaaggaagga gttagacaac ctgaagtcta | 3540 |
| ggtccctatt tatttttta tagttatgtt agtattaaga acgttattta tatttcaaat | 3600 |
| ttttctttt tttctgtaca gacgcgtgta cgcatgtaac attatactga aaaccttgct | 3660 |
| tgagaaggtt ttgggacgct cgaaggcttt aatttgcggc cggtacccaa ttcgccctat | 3720 |
| agtgagtcgt attacgcgcg ctcactggcc gtcgttttac aacgtcgtga ctgggaaaac | 3780 |
| cctggcgtta cccaacttaa tcgccttgca gcacatcccc ctttcgccag ctg | 3833 |

<210> SEQ ID NO 13
<211> LENGTH: 2715
<212> TYPE: DNA
<213> ORGANISM: artificial
<220> FEATURE:
<223> OTHER INFORMATION: expression system comprising synthetic
      nucleotide

<400> SEQUENCE: 13

| | |
|---|---|
| gaattccagc tgtgcttcgg ttacttctaa ggaagtccac acaaatcaag atccgttaga | 60 |
| cgtttcagct tccaaaacag aagaatgtga gaaggcttcc actaaggcta actctcaaca | 120 |
| gacaacaaca cctgcttcat ctgctgttcc agagaaccgc cgacaaccct aatataact | 180 |
| tcgtataatg tatgctatac gaagttatta ggtctagaga tctgtttagc ttgcctcgtc | 240 |

```
cccgccgggt cacccggcca gcgacatgga ggcccagaat accctccttg acagtcttga    300
cgtgcgcagc tcaggggcat gatgtgactg tcgcccgtac atttagccca tacatcccca    360
tgtataatca tttgcatcca tacattttga tggccgcacg gcgcgaagca aaaattacgg    420
ctcctcgctg cagacctgcg agcagggaaa cgctcccctc acagacgcgt tgaattgtcc    480
ccacgccgcg cccctgtaga gaaatataaa aggttaggat ttgccactga ggttcttctt    540
tcatatactt ccttttaaaa tcttgctagg atacagttct cacatcacat ccgaacataa    600
acaaccatgg gtaaggaaaa gactcacgtt tcgaggccgc gattaaattc caacatggat    660
gctgatttat atgggtataa atgggctcgc gataatgtcg ggcaatcagg tgcgacaatc    720
tatcgattgt atgggaagcc cgatgcgcca gagttgtttc tgaaacatgg caaaggtagc    780
gttgccaatg atgttacaga tgagatggtc agactaaact ggctgacgga atttatgcct    840
cttccgacca tcaagcattt tatccgtact cctgatgatg catggttact caccactgcg    900
atccccggca aaacagcatt ccaggtatta gaagaatatc ctgattcagg tgaaaatatt    960
gttgatgcgc tggcagtgtt cctgcgccgg ttgcattcga ttcctgtttg taattgtcct   1020
tttaacagcg atcgcgtatt tcgtctcgct caggcgcaat cacgaatgaa taacggtttg   1080
gttgatgcga gtgattttga tgacgagcgt aatggctggc ctgttgaaca agtctggaaa   1140
gaaatgcata gcttttgcc attctcaccg gattcagtcg tcactcatgg tgatttctca   1200
cttgataacc ttatttttga cgaggggaaa ttaataggtt gtattgatgt tggacgagtc   1260
ggaatcgcag accgatacca ggatcttgcc atcctatgga actgcctcgg tgagttttct   1320
ccttcattac agaaacggct ttttcaaaaa tatggtattg ataatcctga tatgaataaa   1380
ttgcagtttc atttgatgct cgatgagttt ttctaatcag tactgacaat aaaaagattc   1440
ttgttttcaa gaacttgtca tttgtatagt ttttttatat tgtagttgtt ctattttaat   1500
caaatgttag cgtgatttat attttttttc gcctcgacat catctgccca gatgcgaagt   1560
taagtgcgca gaaagtaata tcatgcgtca atcgtatgtg aatgctggtc gctatactgc   1620
tgtcgattcg atactaacgc cgccatccag tgtcgaaaac gagctcaacc cttaatataa   1680
cttcgtataa tgtatgctat acgaagttat taggtcaaaa aactagtctt ttaattctgc   1740
tgtaacccgt acatgcccaa atagggggc gggttacaca gaatatataa catcgtaggt   1800
gtctgggtga acagtttatt cctggcatcc actaaatata atggagcccg cttttaagc   1860 tggcatccag aaaaaaaaag aatcccagca ccaaaatatt gttttcttca ccaaccatca   1920
gttcataggt ccattctctt agcgcaacta cagagaacag gggcacaaac aggcaaaaaa   1980
cgggcacaac ctcaatggag tgatgcaacc tgcctggagt aaatgatgac acaaggcaat   2040
tcacccacgc atgtatctat ctcatttct tacaccttct attaccttct gctctctctg   2100
atttggaaaa agctgaaaaa aaaggttgaa accagttccc tgaaattatt ccctacttg   2160 actaataagt atataaagac ggtaggtatt gattgtaatt ctgtaaatct atttcttaaa   2220
cttcttaaat tctacttta tagttagtct tttttttagt tttaaaacac caagaactta   2280
gtttcgaata aacacacata aacaaacaaa atgagcggcc gcggatccca attgcgactc   2340
gagtaataaa caggccccctt ttcctttgtc gatctcatgt aattagttat gtcacgctta   2400
cattcacgcc ctcctcccac atccgctcta accgaaaagg aaggagttag acaacctgaa   2460
gtctaggtcc ctatttattt tttttaatag ttatgttagt attaagaacg ttatttatat   2520
ttcaaatttt tctttttttt ctgtacaaac gcgacctgat acaagaactt aacaagaaac   2580
caattattaa aggcttactt actgatagta gatcaacgat cagtataatt aagtctacaa   2640
```

```
atgaagagaa atttagaaac agattttttg gcacaaaggc aatgagactt agagatgaag    2700
tatcagctgc tgcag                                                    2715

<210> SEQ ID NO 14
<211> LENGTH: 1225
<212> TYPE: DNA
<213> ORGANISM: artificial
<220> FEATURE:
<223> OTHER INFORMATION: synthetic nucleotide

<400> SEQUENCE: 14
gaattccagc tgtgcttcgg ttacttctaa ggaagtccac acaaatcaag atccgttaga     60
cgtttcagct tccaaaacag aagaatgtga aaggcttcc actaaggcta actctcaaca    120
gacaacaaca cctgcttcat ctgctgttcc agagaaccgt cgacgatatc gagctcaacc    180
cttaatataa cttcgtataa tgtatgctat acgaagttat taggtcaaaa aactagtctt    240
ttaattctgc tgtaacccgt acatgcccaa atagggggc gggttacaca gaatatataa    300
catcgtaggt gtctgggtga acagtttatt cctggcatcc actaaatata atggagcccg    360 cttttttaagc tggcatccag aaaaaaaaag aatcccagca ccaaaatatt gttttcttca    420
ccaaccatca gttcataggt ccattctctt agcgcaacta cagagaacag gggcacaaac    480
aggcaaaaaa cgggcacaac ctcaatggag tgatgcaacc tgcctggagt aaatgatgac    540
acaaggcaat tcacccacgc atgtatctat ctcatttct tacaccttct attaccttct    600
gctctctctg atttggaaaa agctgaaaaa aaaggttgaa accagttccc tgaaattatt    660
cccctacttg actaataagt atataaagac ggtaggtatt gattgtaatt ctgtaaatct    720
atttcttaaa cttcttaaat tctacttttta tagttagtct tttttttagt tttaaaacac    780
caagaactta gtttcgaata acacacata aacaaacaaa atgagcggcc gcggatccca    840
attgcgactc gagtaataaa caggccccctt ttcctttgtc gatctcatgt aattagttat    900
gtcacgctta cattcacgcc ctcctcccac atccgctcta accgaaaagg aaggagttag    960
acaacctgaa gtctaggtcc ctatttattt tttttaatag ttatgttagt attaagaacg   1020
ttatttatat ttcaaatttt tcttttttttt ctgtacaaac gcgacctgat acaagaactt   1080
aacaagaaac caattattaa aggcttactt actgatagta gatcaacgat cagtataatt   1140
aagtctacaa atgaagagaa atttagaaac agattttttg gcacaaaggc aatgagactt   1200
agagatgaag tatcagctgc tgcag                                         1225

<210> SEQ ID NO 15
<211> LENGTH: 1508
<212> TYPE: DNA
<213> ORGANISM: artificial
<220> FEATURE:
<223> OTHER INFORMATION: synthetic nucleotide

<400> SEQUENCE: 15
gtcgacaacc cttaatataa cttcgtataa tgtatgctat acgaagttat taggtctaga     60
gatctgttta gcttgcctcg tccccgccgg gtcacccggc cagcgacatg gaggcccaga    120
ataccctcct tgacagtctt gacgtgcgca gctcaggggc atgatgtgac tgtcgcccgt    180
acatttagcc catacatccc catgtataat catttgcatc catacatttt gatggccgca    240
cggcgcgaag caaaaattac ggctcctcgc tgcagaccty cgagcaggga acgctcccc    300 tcacagacgc gttgaattgt ccccacgccg cgcccctgta gagaaatata aaaggttagg    360
atttgccact gaggttcttc tttcatatac ttccttttaa aatcttgcta ggatacagtt    420
```

-continued

```
ctcacatcac atccgaacat aaacaaccat gggtaaggaa aagactcacg tttcgaggcc      480
gcgattaaat tccaacatgg atgctgattt atatgggtat aaatgggctc gcgataatgt      540
cgggcaatca ggtgcgacaa tctatcgatt gtatgggaag cccgatgcgc cagagttgtt     600
tctgaaacat ggcaaaggta gcgttgccaa tgatgttaca gatgagatgg tcagactaaa      660
ctggctgacg gaatttatgc ctcttccgac catcaagcat tttatccgta ctcctgatga      720
tgcatggtta ctcaccactg cgatccccgg caaaacagca ttccaggtat tagaagaata      780
tcctgattca ggtgaaaata ttgttgatgc gctggcagtg ttcctgcgcc ggttgcattc      840
gattcctgtt tgtaattgtc cttttaacag cgatcgcgta tttcgtctcg ctcaggcgca      900
atcacgaatg aataacggtt tggttgatgc gagtgatttt gatgacgagc gtaatggctg      960
gcctgttgaa caagtctgga aagaaatgca taagcttttg ccattctcac cggattcagt     1020
cgtcactcat ggtgatttct cacttgataa ccttattttt gacgagggga aattaatagg     1080
ttgtattgat gttggacgag tcggaatcgc agaccgatac caggatcttg ccatcctatg     1140
gaactgcctc ggtgagtttt ctccttcatt acagaaacgg cttttcaaa aatatggtat      1200 tgataatcct gatatgaata aattgcagtt tcatttgatg ctcgatgagt ttttctaatc     1260
agtactgaca ataaaaagat tcttgttttc aagaacttgt catttgtata gttttttat      1320 attgtagttg ttctatttta atcaaatgtt agcgtgattt atattttttt tcgcctcgac     1380
atcatctgcc cagatgcgaa gttaagtgcg cagaaagtaa tatcatgcgt caatcgtatg     1440
tgaatgctgg tcgctatact gctgtcgatt cgatactaac gccgccatcc agtgtcgaaa     1500
acgagctc                                                              1508
```

SYSTEM FOR PRODUCING AROMATIC MOLECULES BY BIOCONVERSION

The invention relates to the production of natural aromatic molecules. More particularly, the invention relates to a novel expression system in yeast using an expression cassette and allowing the production of phenolic derivatives by bioconversion, it being possible for said phenolic derivatives to be used for the production of natural aromatic molecules used as food flavoring agents or in perfumery (aromas or fragrances).

The production of natural aromatic molecules can be obtained either via the biological process or by chemical synthesis. For example, vanillin can be obtained by one or the other of these two pathways.

Vanillin (3-methoxy-4-hydroxybenzaldehyde) is the main component responsible for the olfactory and gustative properties of vanilla extract derived from *Vanillia planifolia* pods. It is one of the most commonly used aromatic molecules in the industry. However, the production of natural vanillin from vanilla pods or from vanilla extract covers only 20% of this market; the use thereof is limited owing, firstly, to the potential of pods available worldwide and, secondly, to the high cost of these pods, which fluctuates greatly (of the order of 30 €/kg to 450 €/kg, i.e. a minimum of 1500 €/kg of natural vanillin potential).

Synthetic vanillin is therefore commonly used as a cheap substitute (approximately 15 €/kg) for natural vanillin. However, while synthetic vanillin is suitable for uses in perfumery and in cosmetics, difficulties of the regulatory type can arise in the agrofoods industries. Furthermore, synthetic flavorings are generally less well-liked by consumers than natural flavorings.

For this reason, it is sought to obtain natural aromatic molecules, in particular vanillin, by biological methods, in particular bioconversion methods, which use microorganisms (bacteria, yeasts, molds) or plant cells, or the enzymatic systems thereof.

For the purpose of the present invention, the term "bioconversion" is intended to mean the biological conversion of a substrate, preferably derived from a natural source, so as to obtain natural flavorings, fragrances or precursors of flavorings or of fragrances.

Vanillin can be produced according to the following reaction scheme:

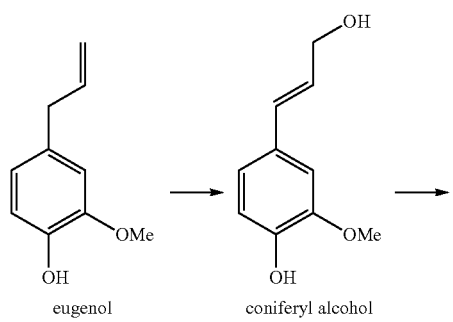

eugenol   coniferyl alcohol

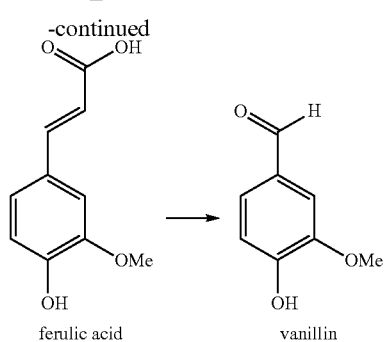

ferulic acid   vanillin

Each of the molecules cited can make it possible to obtain vanillin as long as they are available, the most important being ferulic acid and eugenol.

For example, application EP 453 368, PCT application WO 96/08576 and PCT application WO 00/61721 describe methods for the production of natural vanillin by bioconversion from ferulic acid in the presence of filamentous fungi. The ferulic acid used in these processes originates from the extraction of agricultural coproducts containing ferulic acid esters: corn, rice, beetroot or wheat. However, the low ferulic acid concentration of these coproducts and the multiple steps required for the extraction-purification thereof mean that the extraction yield from these esters remains quite low; thereby generating a high cost for this starting material and therefore a high production cost for the vanillin which derives therefrom.

In order for it to be possible for a biological method using microorganisms to be cost-effective, it is therefore preferable to use a substrate which is more widely available and cheap.

This is the case of eugenol, which can be a source of coniferyl alcohol or of ferulic acid.

The article published by J. Overhage et al. describes the fact that the expression of the vanillyl alcohol oxidase gene derived from *Penicillium simplicissimum*, in *Escherichia coli* makes it possible to catalyze the conversion of eugenol to coniferyl alcohol. To convert the coniferyl alcohol to ferulic acid, J. Overhage et al. subsequently expressed two other *Penicillium simplicissimum*-derived enzymes in *Escherichia coli*: coniferyl alcohol dehydrogenase and coniferyl aldehyde dehydrogenase (Highly efficient biotransformation of eugenol to ferulic acid and further conversion to vanillin in recombinant strains of *Escherichia coli*, 2003, Applied and Environmental microbiology, p. 6569-6576). While this method indeed uses an available and relatively inexpensive substrate, eugenol, this system for producing ferulic acid in *E. coli* remains, however, difficult to implement due to the triple cloning required in order to convert eugenol to ferulic acid.

A subject of the present invention is therefore a method for producing precursors of natural vanillin or natural vanillin itself, at a lower production cost than that of the prior art, and with a method that is simple to implement industrially.

The solutions proposed by the invention are to use or produce available inexpensive natural substrates such as eugenol and ferulic acid. The latter, which is the substrate most commonly used for the synthesis of vanillin, is often expensive and of a quality that is difficult to control.

Another subject of the invention is therefore a simple and efficient method for producing natural ferulic acid and/or natural coniferyl alcohol, the cost of which is industrially acceptable. While ferulic acid can be used as a precursor of natural vanillin, coniferyl alcohol can be a source of dehydroconiferyl alcohol which is encountered in rare fragrances such as that of Tiare flowers and can, via oxidation, be a source of ferulic acid.

The essential means of the methods according to the invention is a yeast comprising at least one gene encoding vanillyl alcohol oxidase, of the vanillyl alcohol oxidase gene type (SEQ ID No. 1) derived from *Penicillium simplicissimum* (Genbank reference Y15627), or any nucleotide sequence having at least 70%, preferably 80%, very preferably 90%, identity with the sequence of SEQ ID No. 1.

Thus, an object of the invention is to propose the bioconversion of inexpensive substrates, in a yeast comprising at least one gene encoding vanillyl alcohol oxidase.

The bioconversion of eugenol by the yeast of the invention allows, on the one hand, the production of natural ferulic acid and/or of natural coniferyl alcohol, without impurities and at low cost, and on the other hand, the production of natural vanillin.

According to one embodiment of the invention, the yeast comprises at least one expression system which contains the gene encoding vanillyl alcohol oxidase. Advantageously, said expression system comprises:

(1) means for integrating said system into the genome of said cell, comprising two nucleotide sequences, (2) means for selecting said cell having integrated said system, comprising a selection insert comprising two LoxP sequences bordering a promoter, a selectable marker of the gene for resistance to antibiotics type, and a terminator, (3) an expression cassette for the gene encoding vanillyl alcohol oxidase, comprising a promoter which allows the expression of said gene, at least one cloning site which allows the integration of said gene, and a terminator.

The term "expression cassette" is intended to mean a nucleotide sequence comprising a promoter, an insertion site for cloning the gene of interest or a multiple cloning site (MCS), and a terminator. The term "promoter" is intended to mean a DNA sequence required for the initiation and the control of transcription, the term "insertion site for cloning" or "multiple cloning site" is intended to mean a DNA sequence containing one or more restriction sites, and the term "terminator" is intended to mean a DNA sequence required for transcription termination. The term "vector" is intended to mean any DNA sequence into which it is possible to insert foreign nucleic acid fragments, the vectors making it possible to introduce foreign DNA into a host cell. Examples of vectors are plasmids, cosmids, yeast artificial chromosomes (YACs), bacterial artificial chromosomes (BACs) and P1 bacteriophage-derived artificial chromosomes (PACs), and virus-derived vectors. The term "selectable marker" is intended to mean a gene, the expression of which confers on the cells which contain it a characteristic which allows them to be selected. It is, for example, a gene for resistance to antibiotics.

According to a preferred embodiment of the invention, the cloning site comprises the restriction sites for the restriction enzymes NotI, BamHI, MfeI and XhoI, allowing the insertion of the vanillyl alcohol oxidase nucleotide sequence into the expression cassette.

Advantageously, the sequence of this cloning site is the sequence SEQ ID No. 2 or any sequence at least 70%, preferably 80%, very preferably 90%, homologous to the sequence SEQ ID No. 2.

According to a preferred embodiment of the invention, the bordering of the selectable marker with two LoxP sites will allow this selectable marker to be excised by virtue of the CRE/Lox system. The CRE enzyme is a recombinase which specifically recognizes LoxP sites. The nucleotide sequence between these two sites is referred to as target DNA and will be removed in the presence of the CRE enzyme. This is because, when the CRE enzyme binds to the LoxP sites, it cuts these sites in two and sticks two halves back together after the target DNA has been removed.

Advantageously, the sequence of the LoxP sequences is the sequence SEQ ID No. 3 or any sequence at least 70%, preferably 80%, very preferably 90%, homologous to the sequence SEQ ID No. 3.

According to a preferred embodiment of the present invention, the sequences which allow the integration of the expression system into the genome of said yeast are multiple and are chosen from the group comprising TY sequences, telomeric sequences X and Y', DUP sequences, the sequence □ or any sequences that are repeated in genome of the yeast.

Advantageously, said sequences are the TY1A and TY1B sequences of *Saccharomyces cerevisiae*, the sequence of which is preferably the sequences SEQ ID No. 4 and SEQ ID No. 5, respectively, or any sequences which are at least 70%, preferably 80%, very preferably 90%, homologous thereto.

According to another preferred embodiment of the invention, the promoters used in the expression system are strong promoters, i.e. promoters which induce a strong transcription of the genes under their control. Examples of strong promoters are 1) promoters controlling the expression of genes the proteins of which are abundant in the yeast, such as promoters controlling the expression of glycolysis proteins or nitrogen metabolism proteins; 2) promoters the expression of which is specific, for example promoters of which the activity is regulated by the presence of sugar or of nitrogen; 3) promoters the activity of which is high in view of transcriptome experiments; or 4) artificial promoters designed to allow strong transcription of the genes that they regulate. The terminators used in the expression system are chosen for their ability to allow good mRNA stability. Advantageously, the terminator chosen corresponds to the strong promoter chosen above.

Advantageously, the promoter which allows the expression of the gene of interest in the expression system is the promoter of the *Saccharomyces cerevisiae* TDH3 gene, the sequence of which is preferably the sequence SEQ ID No. 6 or any sequence at least 70%, preferably 80%, very preferably 90%, homologous to the sequence SEQ ID No. 6.

Advantageously, the associated terminator is the terminator of the *Saccharomyces cerevisiae* CYC1 gene, the sequence of which is preferably the sequence SEQ ID No. 7 or any sequence at least 70%, preferably 80%, very preferably 90%, homologous to the sequence SEQ ID No. 7.

Advantageously, the promoter and the terminator which allow the expression of the selectable marker are the promoter and the terminator of the *Ashbya gossypii* TEF1 gene, the sequence of which is preferably the sequence SEQ ID No. 8 and SEQ ID No. 9, respectively, or any sequences which are at least 70%, preferably 80%, very preferably 90%, homologous thereto.

According to another preferred embodiment of the invention, the selectable marker used in the expression system is a gene for resistance to antibiotics, chosen from the group comprising the genes for resistance to geneticin, nourseothricin, phleomycin or zeocin, or any other gene for resistance to a dominant antibiotic to which the wild-type yeast is sensitive.

Advantageously, the selectable marker used in the expression system is the geneticin-resistance gene, the sequence of which is preferably the sequence SEQ ID No. 10 or any sequence at least 70%, preferably 80%, very preferably 90%, homologous to the sequence SEQ ID No. 10.

According to another preferred embodiment of the invention, the sequence of the expression system containing the vanillyl alcohol oxidase gene is the nucleotide sequence of SEQ ID No. 11 or any sequence at least 70%, preferably 80%, very preferably 90%, homologous to the sequence SEQ ID No. 11.

A subject of the present invention is also a vector comprising an expression system as defined above.

According to another preferred embodiment of the invention, the vector comprising the expression system is a plasmid, and advantageously pUC57.

The invention also encompasses transformed bacteria comprising at least one vector as defined above.

These transformed bacteria may belong to any species which allows the replication of the chosen carrier vector. Advantageously, these are bacteria of the *E. coli* genus.

A subject of the present invention is also a vector for excision of the gene for resistance to antibiotics, said excision vector comprising:

(1) means for selecting the cells containing it, comprising the promoter and the terminator of the *Ashbya gossypii* TEF1 gene and the nourseothricin-resistance gene, and (2) means for excising the selectable marker present in the expression system, comprising the promoter of the *Saccharomyces cerevisiae* GAL1 gene, the CRE gene and the terminator of the *Saccharomyces cerevisiae* CYC1 gene.

Advantageously, the excision vector comprises the sequence SEQ ID No. 12 or any sequence at least 70%, preferably 80%, very preferably 90%, homologous to the sequence SEQ ID No. 12.

According to a preferred embodiment of the invention, the excision vector described above is chosen from vectors which are poorly segregated during cell divisions, resulting, through this characteristic, in a loss of the vector in the absence of frequent selection pressure, for example multicopy replicative vectors.

Advantageously, the excision vector is the plasmid pFL44s.

The first advantage of this excision vector is that it allows the gene for resistance to antibiotics which is present in the genome of the yeasts to be eliminated following the transformation of said yeasts with the expression system. The yeasts allowing the production of aromatic molecules according to the invention do not therefore contain any DNA which does not originate from strains belonging to the same genus or to the same family, with the exception of the gene encoding vanillyl alcohol oxidase.

Furthermore, the elimination of the resistance gene by means of the excision vector also makes it possible to transform a yeast several times, so as to increase the number of copies of the expression system present in the genome and thus to increase the amount of vanillyl alcohol oxidase protein produced.

A subject of the invention is yeasts comprising the expression system containing vanillyl alcohol oxidase, the sequence of said expression system being the sequence SEQ ID No. 11 or any sequence at least 70%, preferably 80%, very preferably 90%, homologous to the sequence SEQ ID No. 11.

A subject of the invention is also yeasts as described above and/or transformed with the excision vector as described above.

According to a preferred embodiment of the invention, the yeasts belong to any species of yeasts capable of carrying out the bioconversion of the vanillin precursors (in particular eugenol, ferulic acid, coniferyl alcohol) to vanillin according to known prior art methods.

For the purpose of the present invention, the term "yeasts" is intended to mean any diploid or polyploid yeast or any haploid clone derived from the sporulation of one of these strains, or alternatively any diploid clone derived from the crossing of two haploid clones.

Advantageously, the yeasts belong to any species of hemiascomycete yeast, preferably to the *Saccharomyces* genus or hybrids thereof. Very preferably, the yeasts originate from a *Cerevisiae* strain or hybrids thereof.

A subject of the present invention is a method for producing natural coniferyl alcohol and/or natural ferulic acid, comprising the following steps:

a) cloning the nucleotide sequence of the gene encoding vanillyl alcohol oxidase into the expression system,
b) transforming the yeast with the expression system thus obtained,
c) culturing the yeast under the conditions which allow the expression of the vanillyl alcohol oxidase,
d) bringing the yeast into contact with eugenol.

According to a preferred embodiment of the invention, the nucleotide sequence of the gene encoding vanillyl alcohol oxidase and the vector comprising the expression system are initially digested with one or more restriction enzymes. The sequence of the gene encoding vanillyl alcohol oxidase is subsequently inserted, by simple ligation or any other insertion means, into the expression system carried by the vector.

To amplify the expression system, bacteria are transformed with the ligation product (vector carrying the expression system containing the vanillyl alcohol oxidase gene) according to any method. The bacteria having integrated the expression system are selected by virtue of the gene for resistance to antibiotics present on the vector carrying the expression system containing the gene encoding vanillyl alcohol oxidase.

Secondly, the vector carrying the expression system is digested with one or more restriction enzymes, preferably PvuII, which cleave(s) on either side of the expression system. The expression system is subsequently purified and then used to transform the yeasts according to any known method. The yeasts having integrated the expression system are selected by virtue of the resistance gene present in the expression system.

Finally, the transformed yeasts are cultured under the conditions known to those skilled in the art which allow the expression of vanillyl alcohol oxidase. When the eugenol is added to the culture, the vanillyl alcohol oxidase makes it possible to catalyze the bioconversion of said eugenol to coniferyl alcohol and/or to ferulic acid.

A subject of the invention is also a method for producing natural coniferyl alcohol and/or natural ferulic acid, in which the selectable marker present in the genome of the yeast has been excised, said method comprising, after step b) and before steps c) and d), the following steps b1), b2) and b3):

b1) transforming the yeast with the excision vector,
b2) culturing the yeast under the conditions which allow the expression of the CRE system,
b3) isolating the yeasts having lost the selectable marker.

According to a preferred embodiment of the invention, the nucleotide sequence of the gene encoding vanillyl alcohol oxidase is inserted into the expression system, and the yeasts are firstly transformed with this expression system as described above. The yeasts having integrated the expression system are selected by virtue of the presence of a first selectable marker, preferably a gene for resistance to antibiotics. The positively selected yeasts are subsequently transformed with the excision vector according to any known method. The yeasts having integrated the excision vector are selected by virtue of the nourseothricin-resistance gene present in the excision vector.

The yeasts, having therefore integrated the expression system and the excision vector, are then cultured under the conditions which allow the expression of the CRE enzyme. The active CRE enzyme will make it possible to excise the first selectable marker bordered by the loxP sequences in the expression system. The yeasts having lost this selectable marker are subsequently selected. For example, the yeasts having lost this first gene for resistance to an antibiotic are selected by virtue of their lack of resistance to this antibiotic.

The yeasts obtained following this selection step no longer possess the selectable marker present in the expression system, but still possess the nourseothricin-resistance gene present in the excision vector. As described above, the excision vector is chosen from vectors which are poorly segregated during cell divisions. By virtue of this characteristic, the excision vector is readily lost in the absence of frequent selection pressure. The term "selection pressure" is intended to mean any method which contributes to selecting the cells. For example, maintaining in culture yeasts which possess a gene for resistance to an antibiotic, in the presence of this antibiotic, corresponds to a method of selection pressure. The yeasts obtained in the preceding step are therefore cultured in the absence of selection pressure so as to lose the excision vector, and are then selected for the loss of the nourseothricin-resistance gene.

The yeasts thus obtained have integrated into their genome the expression system which allows the expression of vanillyl alcohol oxidase, while their genome no longer contains any genes for resistance to antibiotics. The transformed yeasts are then cultured under the conditions, known to those skilled in the art, which allow the expression of vanillyl alcohol oxidase. When eugenol is added to the culture, the vanillyl alcohol oxidase makes it possible to catalyze the bioconversion of said eugenol to coniferyl alcohol and/or to ferulic acid.

Finally, a subject of the invention is also a method for producing natural coniferyl alcohol and/or natural ferulic acid, in which steps b), b1), b2) and b3) are repeated as many times as the desired number of copies of the expression system, with the aim of increasing the number of copies of the expression system in the genome of the yeast.

According to a preferred embodiment of the invention, the yeasts are firstly transformed with the expression system and then selected as described above. These yeasts are subsequently transformed with the excision vector, so as to allow the elimination of the selectable marker as described above. The yeasts thus obtained no longer possess the selectable marker in their genome and have integrated at least one copy of the expression system.

Secondly, in order to increase the number of copies of the expression system, these yeasts are again transformed with the expression system. The same method of selection, of transformation with the excision vector and of final selection is carried out as above. The yeasts thus obtained no longer possess selectable markers and have integrated into their genome at least two copies of the expression system. This method can be repeated as many times as desired.

A subject of the present invention is a method for producing vanillin, comprising steps a), b), c) and d) as described above and a subsequent step of converting the ferulic acid and/or the coniferyl alcohol, produced in step d), to vanillin.

According to a preferred embodiment of the invention, the yeast, by virtue of its own genetic material, is capable of converting the ferulic acid produced in step d), to vanillin.

According to another preferred embodiment of the invention, the step of converting the ferulic acid and/or the coniferyl alcohol to vanillin is carried out by enzymatic process or biochemical process according to the methods described in patents EP 0 606 441 and EP 0 804 606.

The present invention will be understood more clearly from the further description which will follow, which refers to examples of obtaining the expression system comprising vanillyl alcohol oxidase, vectors comprising this expression system, excision vectors, and the use thereof for the production of coniferyl alcohol and of ferulic acid by bioconversion of eugenol.

Figure 2:
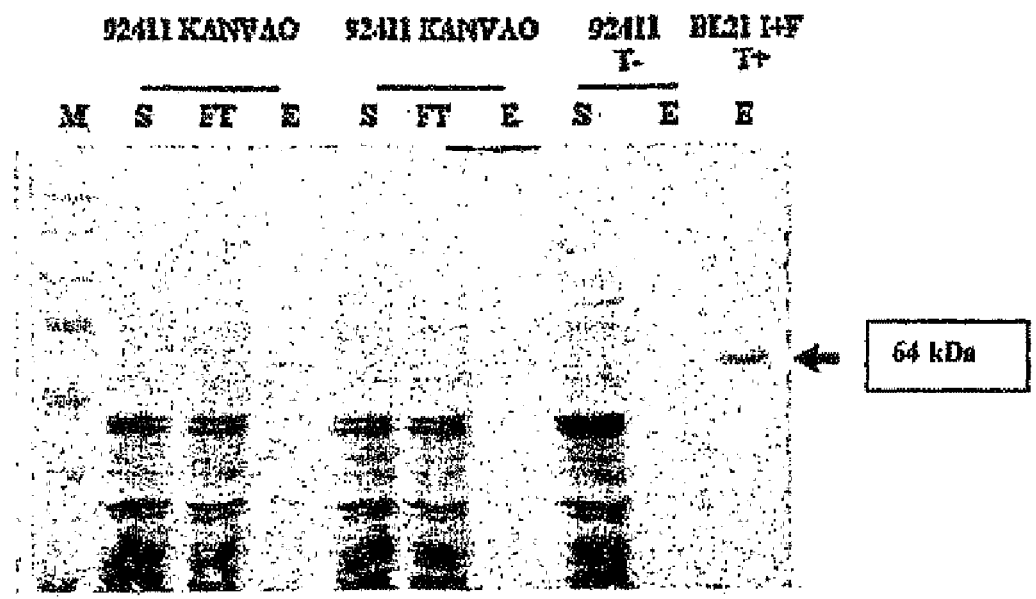
Figure 3:
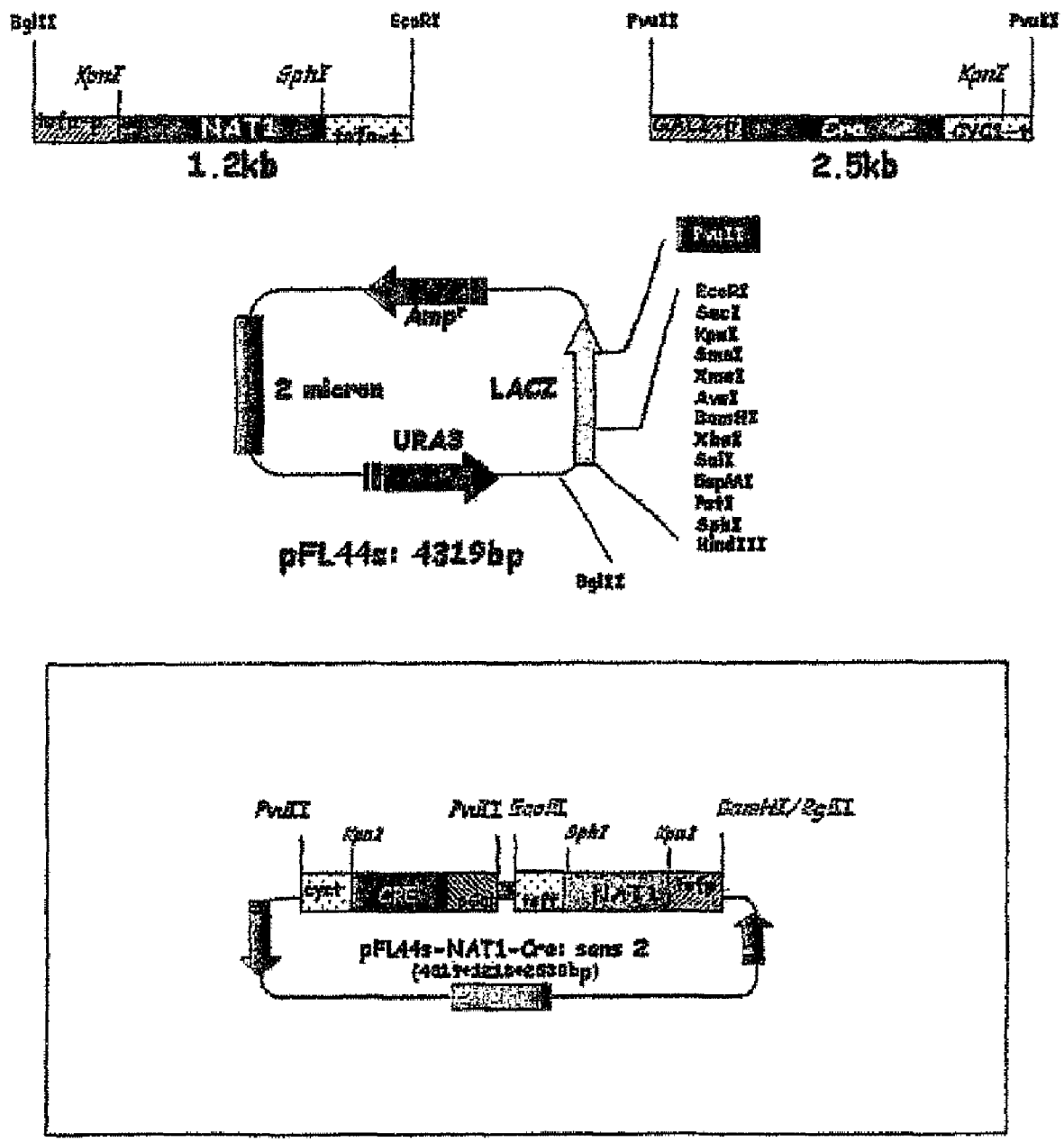

In the examples which follow, given by way of illustration, reference will be made to the figures attached in the annex, in which:

FIG. 1 presents a scheme of the expression system,

FIG. 2 presents the expression of vanillyl alcohol oxidase by the yeasts,

FIG. 3 presents the method for obtaining the excision vector pFL44s-NAT1-CRE.

EXAMPLE 1

Expression of Vanillyl Alcohol Oxidase in the Yeast by Transformation of the Yeast with the Expression System 1/ Synthesis of the Expression System The expression system comprises the nucleotide sequence of 2715 bp described in SEQ ID No. 13. This nucleotide sequence was constructed from a synthetic sequence (SEQ ID No. 14) and a selection insert (SEQ ID No. 15).

The synthetic sequence has a size of 1225 bp and was synthesized by GenScript Corporation. This sequence comprises:
 the TY1A sequence
 an LoxP sequence
 the sequence of the promoter of the TDH3 gene
 a multiple cloning site sequence
 the sequence of the terminator of the CYC1 gene
 the TY1B sequence.

The selection insert was isolated from the vector pUG6 cloned into *E. coli* (Güldener, U., Heck, S., Fiedler, T., Beinhauer, J., and Hegemann, J. H. 1996. A new efficient gene disruption cassette for repeated use in budding yeast. Nucleic Acids Res. 24: 2519-2524). The selection insert contains 1500 bp and comprises:
 an loxP sequence
 the sequence of the promoter of the TEF1 gene
 the sequence of the kan$^r$ gene
 the sequence of the terminator of the TEF1 gene.

This insert was isolated by digestion of the pUG6 vector with the SalI and SacI restriction enzymes.

The expression system comprising the synthetic sequence was cloned into the pUC57 vector (GenScript Corporation) by virtue of the EcoRI and PstI restriction sites.

The pUG6 vector and the pUC57 vector containing the expression system were digested with the SalI and SacI restriction enzymes. The selection insert is subsequently inserted by simple ligation into the synthetic sequence between TY1A and the LoxP sequence located on either side of the SalI and SacI restriction sites.

The vector thus obtained, comprising the expression system (synthetic sequence+selection insert), is called pM2-KAN (FIG. 1).

The XbaI and SacI restriction sites present in the selection insert make it possible to change the selectable marker and its expression sequences if the user so desired.

The SalI and SpeI restriction sites make it possible to remove or replace all the sequences made up of the selectable marker and its expression sequences, bordered by the two LoxP sequences.

2/ Insertion of the Gene Encoding Vanillyl Alcohol Oxidase into the Expression System The nucleotide sequence of the VAO is derived from *Penicillium simplicissium* (Genbank reference Y15627). The VAO sequence (SEQ ID No. 1) used in this experiment was synthesized with a NotI site in the 5' position and an XhoI site in the 3' position, so as to allow it to be cloned into the pivex vector, this cloning being in-frame with a nucleotide sequence for producing a protein with a C-terminal six-histidine tag.

The pivex vector containing the VAO sequence as described above was digested with NotI and EcoRI so as to release the VAO-6His sequence. This sequence is subsequently cloned by simple ligation into the pUC57 vector containing the expression system digested beforehand with NotI and MfeI.

3/ Transformation of the Yeasts with the Expression System Comprising the Gene Encoding Vanillyl Alcohol Oxidase The pUC57 vector containing the expression system is digested with the PvuII restriction enzyme. This enzyme cleaves on either side of the expression system containing the gene of interest: VAO. The DNA fragment derived from this digestion is purified and used to transform the yeasts according to a heat-shock method in the presence of PEG/lithium acetate.

The transformed yeasts are selected, by virtue of the presence of the KANr resistance gene carried by the expression system, on YPD rich medium (1% yeast extract, 1% peptone, 2% glucose) containing 300 mg/l of geneticin.

Twenty-four clones of *Saccharomyces cerevisiae* yeasts (strain 92411) were obtained after transformation (clones 92411 KANVAO).

4/ Analysis of the Expression of Vanillyl Alcohol Oxidase by the Transformed Yeasts The transformed yeasts are cultured on complete glucose-containing medium (YPD). The VAO protein is subsequently affinity-purified on Ni NTA resin as in example 1. The proteins retained on the resin are analyzed by polyacrylamide gel electrophoresis (SDS-PAGE gel) and detected with coomassie blue. FIG. 2 shows, for two clones, that the VAO protein is produced (columns E 92411 KANVAO). The 92411 T– clone corresponds to the negative control, i.e. to a nontransformed 92411 strain, and does not produce any VAO protein, while BL21 I+F corresponds to a positive control resulting from the cloning of the vanillyl VAO in the pivex vector and from the production thereof in *E. coli*.

EXAMPLE 2

Production of Coniferyl Alcohol and of Ferulic Acid by Bioconversion of Eugenol in the Yeasts Expressing Vanillyl Alcohol Oxidase The yeasts transformed with the expression system containing vanillyl alcohol oxidase, as described above, were selected first of all for their ability to convert eugenol to coniferyl alcohol, and then some of them were selected for their ability to produce ferulic acid. Thus, the 93205 clone, preselected for its ability to form coniferyl alcohol, was found to be subsequently capable, via its derivatives, of converting eugenol to ferulic acid.

The 93207 clone and the progeny thereof were chosen as examples of strains capable of converting eugenol to coniferyl alcohol in a fermenter.

1/ Production of Coniferyl Alcohol in a Fermenter with the 93207 Strain and a Derivative Thereof, 93334

Two spores of the 93207 strain were crossed to give the diploid strain 93334, which thus comprises two copies of the expression system containing vanillyl alcohol oxidase.

The 93334 strain is subsequently cultured in 100 ml of malt medium for two days so as to reach a concentration of approximately 3 to $6 \times 10^8$ cells/ml. The cells are subsequently inoculated into a fermenter containing 3 liters of malt medium. The inoculation is carried out with half the volume of preculture, at 30° C. and with shaking at 500 rpm. The aeration is brought to 1 liter of air/minute.

After culturing for 20 h, the eugenol is added in solution in 50% glucose (60 g of eugenol+120 ml of glucose at 50% in $H_2O$).

After 18 h of conversion, the fermentation is stopped. A sample is taken. It is acidified with phosphoric acid, diluted 2-fold in ethanol and centrifuged at 8000 rpm. The supernatant is analyzed by HPLC.

The results show that, in 18 hours, the eugenol is virtually completely converted and that 22 g/l of coniferyl alcohol were synthesized (molar yield close to 100%).

2/ Production of Ferulic Acid in a Fermenter with the 93205 Strain and a Derivative Thereof, 93342

The haploid strain 93242, derived from sporulation of the 93205 strain, is cultured in 100 ml of malt medium for two days, with shaking (150 rpm) and at 30° C. The cells are subsequently cultured in a fermenter in 3 liters of malt medium. The inoculation is carried out with half the volume of preculture, with shaking (500 rpm) and at 30° C. The aeration is brought to 0.45 liter of air/minute for 24 h.

After culturing for 24 h, the solution of eugenol is added continuously with a flow rate of 0.25 to 0.5 g of eugenol per hour.

Samples are taken regularly in order to monitor the conversion of the substrate to phenolic derivatives. Each sample is acidified with phosphoric acid and centrifuged at 8000 rpm. The supernatant is analyzed by HPLC.

Substrate Flow Rate: 2.5 ml/H

Concentrations in Gram Per Liter

| Time (hours) | Eugenol distributed | Eugenol remaining | Coniferyl alcohol | Ferulic acid |
|---|---|---|---|---|
| 0 | 0 | 0 | 0 | 0 |
| 16 | 1.6 | 0 | 0.7 | 0.75 |
| 40 | 3.8 | 0 | 0 | 3.8 |
| 64 | 7.1 | 0 | 0.2 | 6.7 |
| 112 | 10 | 0 | 0 | 10.11 |

Under these conditions, 10 g/l of ferulic acid are produced from 10 g/l of eugenol (molar yield = 85%).

EXAMPLE 3

Excision of the Selectable Marker from the Genome of the Transformed Yeasts

1/ Construction of the pFL44s-NAT1-CRE Vector for Excision of the Selectable Marker The vector of origin for the excision vector is, in this example, the pFL44s vector (Genbank reference X70266). This vector, 4319 bp in length, has:
  the sequence of the URA3 gene
  the sequence of the AmpR resistance gene
  a multiple cloning site
  the sequence of the 2 micron origin of replication.

An insert comprising a selectable marker and an insert comprising the sequence of the CRE enzyme are inserted into this PFL44s vector.

The insert comprising the selectable marker, which here is the nourseothricin-resistance gene NAT1, is obtained from the vector encoding nourseothricin (Genbank reference X73149). Said vector and the pFL44s vector are digested with the BglII and EcoRI restriction enzyme. The NAT1 insert comprising the promoter of the TEF gene, the sequence of the NAT1 gene and the terminator of the TEF gene, is inserted by simple ligation into the pFL44s vector. The vector thus obtained is the pFL44s-NAT1 vector.

The insert comprising the sequence of the CRE enzyme is obtained from the psh47 vector (Genbank reference AF298782). The psh47 vector and the pFL44s-NAT1 vector are digested with the PvuII restriction enzyme. The CRE insert comprising the promoter of the GAL1 gene, the CRE gene sequence and the terminator of the CYC1 gene, is subsequently inserted by simple ligation into the pFL44s-NAT1 vector. The vector thus obtained is the pFL44s-NAT1-CRE vector, the sequence of which is the sequence SEQ ID No. 11 (FIG. 3).

2/ Transformation of the Yeasts with the Excision Vector for Removing the Selectable Marker Present in the Yeast Genome The yeasts comprising the expression system containing vanillyl alcohol oxidase, for example the 93334 strain, are transformed with the pFL44s-NAT1-CRE excision vector. The transformed yeasts are selected on rich medium (YPD) supplemented with clonNAT (100 mg/ml).

The positively selected yeasts are subsequently cultured in a YPGalactose medium. Since the promoter of the CRE gene is inducible in the presence of galactose, this culture condition makes it possible to induce the expression of the CRE enzyme in the yeasts.

The results of this experiment show that 80% of the clones have lost the KanR marker.

The method for converting eugenol to coniferyl alcohol as described in 1/ is carried out with a 93334 strain having lost the selectable marker. After 18 h of conversion, the same results are obtained, suggesting that the loss of the selectable marker does not affect the bioconversion capacity of the strain.

The invention claimed is:

1. A recombinant yeast, comprising at least one gene encoding vanillyl alcohol oxidase, the at least one gene comprising the nucleic acid sequence of SEQ ID No. 1 or any sequence at least 90% homologous to the sequence SEQ ID No. 1.

2. The recombinant yeast as claimed in claim 1, wherein the gene encoding vanillyl alcohol oxidase is contained in an expression system, said expression system comprising:
   (1) a means for integrating said expression system into a genome of said yeast, comprising two nucleotide sequences,
   (2) a means for selecting said yeast having integrated said system, comprising a selection insert comprising two LoxP sequences, each LoxP comprising sequence SEQ ID No. 3, bordering a promoter, a selectable marker comprising a gene for resistance to antibiotics, and a terminator,
   (3) an expression cassette for the gene encoding vanillyl alcohol oxidase, comprising a promoter which allows expression of said vanillyl alcohol oxidase gene, at least one cloning site which allows integration of the vanillyl alcohol oxidase gene into the genome of the yeast, and a terminator.

3. The recombinant yeast as claimed in claim 2, wherein the two nucleotide sequences for integration of said expression system into the genome of the yeast are a TY1A sequence corresponding to SEQ ID No. 4 and a TY1B sequence corresponding to SEQ ID No. 5, or any sequences which are at least 90% homologous thereto.

4. The recombinant yeast as claimed in claim 2, wherein the promoter which allows the expression of the vanillyl alcohol oxidase gene is the promoter of a *Saccharomyces cerevisiae* TDH3 gene (SEQ ID No. 6), and the associated terminator is the terminator of a *Saccharomyces cerevisiae* CYC1 gene (SEQ ID No. 7), or any sequences which are at least 90% homologous thereto.

5. The recombinant yeast as claimed in claim 2, wherein the promoter and the terminator which allow expression of the selectable marker are the promoter of a *Ashbya gossypii* TEF1 gene (SEQ ID No. 8) and the terminator of a *Ashbya gossypii* TEF1 gene (SEQ ID No. 9) or any sequences which are at least 90% homologous thereto.

6. The recombinant yeast as claimed in claim 2, wherein the selectable marker is a gene for resistance to an antibiotic, the antibiotic selected from the group consisting of: geneticin, nourseothricin, phleomycin and zeocin, or any other gene for resistance to a dominant antibiotic to which the wild-type yeast is sensitive.

7. The recombinant yeast as claimed in claim 2, wherein the expression system containing the vanillyl alcohol oxidase gene comprises the nucleotide sequence SEQ ID No. 11 or any sequence which is at least 90% homologous thereto.

8. The recombinant yeast as claimed in claim 1, wherein the yeast belongs to any species of yeasts capable of carrying out a bioconversion of vanillin precursors to vanillin.

9. The recombinant yeast as claimed in claim 1, wherein the yeast belongs to any species of hemiascomycetes yeasts.

10. A vector or a plasmid comprising the expression system as claimed in claim 2.

11. A bacterium comprising the vector as claimed in claim 10.

12. A method for producing natural coniferyl alcohol and/or natural ferulic acid, comprising the following steps:

a) cloning a nucleotide sequence of a gene encoding vanillyl alcohol oxidase into the expression system as defined in claim 2, b) transforming yeast with the expression system obtained in step a), c) culturing the yeast under conditions which allow expression of the vanillyl alcohol oxidase gene, d) bringing the yeast into contact with eugenol to produce the coniferyl alcohol and/or ferulic acid.

13. The method for producing vanillin, comprising steps a), b), c) and d) as described in claim 12, further comprising a step of converting the ferulic acid and/or the coniferyl alcohol, produced in step d), to vanillin.

14. The method for producing vanillin as claimed in claim 13, wherein the step of converting the ferulic acid and/or the coniferyl alcohol, produced in step d), to vanillin is carried out in a yeast or by biochemical process or enzymatic process.

15. The recombinant yeast as claimed in claim 1, wherein the yeast is *Saccharomyces* or hybrids thereof.

16. The recombinant yeast as claimed in claim 1, wherein the yeast is *Saccharomyces cerevisiae* or hybrids thereof.

17. The bacterium as claimed in claim 11, wherein the vector is pUC57 and the bacterium is *E. coli*.

18. A recombinant yeast, comprising at least one gene encoding vanillyl alcohol oxidase, the at least one gene comprising the nucleic acid sequence of SEQ ID No. 1.

* * * * *

UNITED STATES PATENT AND TRADEMARK OFFICE
CERTIFICATE OF CORRECTION

PATENT NO.       : 8,404,472 B2                                    Page 1 of 1
APPLICATION NO.  : 12/281405
DATED            : March 26, 2013
INVENTOR(S)      : Zucca et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 872 days.

Signed and Sealed this
First Day of September, 2015

Michelle K. Lee
*Director of the United States Patent and Trademark Office*